United States Patent [19]

Hirsch

[11] Patent Number: 5,759,521
[45] Date of Patent: Jun. 2, 1998

[54] METHOD OF ALTERING PERCEPTION OF RELATIVE SPACE OF AN AREA

[76] Inventor: Alan R. Hirsch, 180 E. Pearson #4702, Chicago, Ill. 60611

[21] Appl. No.: 557,528

[22] Filed: Nov. 14, 1995

[51] Int. Cl.$^6$ .............................. A61K 7/00; A61K 7/46
[52] U.S. Cl. .................................. 424/47; 514/957
[58] Field of Search ................. 514/957; 424/47

[56] References Cited

U.S. PATENT DOCUMENTS

| | | | |
|---|---|---|---|
| 4,671,959 | 6/1987 | Warren et al. | 424/195.1 |
| 5,382,567 | 1/1995 | Fuwa et al. | 512/4 |

OTHER PUBLICATIONS

Buchbauer, G., Z. Naturforsch Sect C Biosci., 46(11-12):107-1072, 1991.

Komori, T., Neuroimmunomodulation, 2(3):174-180, 1995.

J. Borden, "This story stinks, but it might be quite lucrative," Chicago Business Crain's, Metro Chicago's Business Authority (Dec. 2-8, 1991).

Hirsch et al., Amer. Psych. Assn., 1995 Annual Meeting (Miami, Florida), Abstract NR398 ("Odors and Perceptions of Room Size")(May 20-25, 1995).

Ludvigson & Rottman, Chemical Senses 14:525-536 (1989).

Erlichman, H. and Bastone, L., "Olfaction and Emotion", Science of Olfaction, pp. 410-417, Serby and Choboro (Eds.), Springer-Verlag, New York, NY (1992).

Erlichman, H. and Bastone, L., Perfumer & Flavorist 16:11-12 (1991).

P.D. MacLean, "Cerebral evolution of emotion," in Lewis and Haviland (eds.), Handbook of Emotions, p. 77, The Guilford Press, New York, NY (1993).

H. Sugano, JASTS 12-8 (Abstract) (1988).

A.R. Hirsch, Advances in Consumer Research 19:390-395 (1992).

J.R. King, "Anxiety Reduction Using Fragrances," in Perfumery, The Psychology and Biology of Fragrance, pp. 147-165, Van Toller & Dodd (eds.), Chapman and Hall, Ltd., London (1988).

Hirsch et al., Chemical Senses 17:643 (1992) (AChemS XIV Abstracts 124-128).

Amoore et al., Rhinology 21:49-54 (1983).

Doty et al., Chemical Senses 10:297-300 (1985).

W.W.K. Zung, Arch. Gen. Psychiatry 12:63-70 (1965).

W.W.K. Zung, Psychosomatics 12(6):371-379 (1971).

C.B. Scrignar, "Stress Strategies," in The Treatment of Anxiety Disorders, pp. 6-8, Andrews et al. (eds.), Cambridge Univ. Press, New York, NY (1994).

Clarke et al., Hypnosis and Behavior Therapy, The Treatment of Anxiety and Phobias, pp. 320-321, Clark and Jackson (eds.), Springer Publishing Company, New York, NY (1983).

World Psychiatric Association, Panic Anxiety and its Treatments, p. 7, Klerman et al. (eds.), American Psychiatric Press, Inc., Washington, D.C. (1993).

Rachman and Taylor, J. Anxiety Disorders, 7:281-291 (1993).

Primary Examiner—Marianne P. Allen
Attorney, Agent, or Firm—Godfrey & Kahn, S.C.

[57] ABSTRACT

The present invention provides a method for altering a person's perception of a confined or open space by administering an odorant substance to the person.

18 Claims, No Drawings

METHOD OF ALTERING PERCEPTION OF RELATIVE SPACE OF AN AREA

BACKGROUND OF THE INVENTION

Individual tolerance of spatial size varies from the extremes of claustrophobia (the fear of closed or narrow spaces) to agoraphobia (the fear of open spaces). The everyday lives of persons with spatial anxiety can be dramatically affected. Those with severe claustrophobia fear everyday activities such as riding in elevators, buses, and subways. Those with agoraphobia may have difficulty leaving their homes. Claustrophobia, based on community samples, ranges from about 10 to 11.3%. The calculated lifetime prevalence of agoraphobia is between about 0.5% and 1.7%. A person with claustrophobia or agoraphobia experiences panic attacks when in a small, confined area or in an open space, respectively. The panic attack can result in a physiological response including an increased heart rate, sweaty palms, trembling and shortness of breath.

Entire courses in interior design and architecture have focused upon influencing perceptions of surrounding space, and countless resources are spent to expand cramped offices and shrink vast convention halls. Visually, a cramped room can be enlarged, for example, through the use of mirrors, windows and/or natural light, and by positioning furniture along the periphery. The visual image can also be used to lessen the expanse of a large room, for example, by using curtains, dim lights and/or ornate designs, and by placing furniture in the middle of the room.

Auditory stimuli, such as echoes, can also affect judgment of room size. Bare walls that increase echoes can make a room seem larger. In contrast, carpets and padded walls can dampen sound and make the room seem smaller.

The sensation of touch can also influence perceived room size. Hardwood floors can enlarge a small interior while plush carpeting and oversized furniture can decrease the expanse of larger interiors.

Perceptions of room size can also be influenced by temperature. A warm fireplace can impart a cozy feeling in a large living room. An extreme temperature, such as a frigid parking garage in winter, can increase feelings of solitude and emptiness. In contrast, an oppressive summer heat can induce a feeling of confinement, particularly when stalled in a traffic jam.

Although such design changes can alter a person's perception of room size to lessen the feelings of claustrophobia and agoraphobia, persons suffering from such ailments cannot rely on such alterations in every instance. Therefore, an object of the invention is to provide a means to enable a person suffering from a spatial tolerance disorder to better tolerate a closed/narrow space or open space. Another object of the invention is to provide such means in a form that is portable and can be carried by the individual for ready access and use.

SUMMARY OF THE INVENTION

The present invention provides a method for treating a patient having a spatial dissonance by administering an odorant substance that will alter the patient's perception of relative space of an area. An odorant substance can be administered to expand a person's perception of a cramped and/or confined space or to diminish his or her perception of a wide or vast space.

According to the invention, a substance having the characteristics of a green apple odorant, cucumber odorant, or seashore odorant is administered to a patient to cause the patient's perception of a confined area to become altered and expanded, preferably using a green apple odorant. The invention further includes administering a substance having the characteristics of a barbecue smoke odorant to a patient to cause the patient's perception of an open area to become altered and diminished.

The introduction of a space perception altering odorant can be used to decrease the anxiety felt by claustrophobic and agoraphobic persons and thereby help them to more easily assimilate into an everyday environment. The introduction of a space perception altering odorant can also be used to comfort persons who do not have the extreme anxiety characteristic of claustrophobia or agoraphobia, but experience a mild spatial dissonance, by modifying the ambience of everyday surroundings and changing their perception of relative space.

DETAILED DESCRIPTION OF THE INVENTION

According to the invention, it was found that the administration of a green apple odorant substance will expand the perception of room size for a person suffering from claustrophobia. In particular, it was found that a green apple odorant can decrease the anxiety in a person suffering from claustrophobia, or other like phobia, and/or reduce the stress experienced by a person with mild spatial dissonance of closed or narrow space. Examples of such confined spaces include an enclosed room, closet, telephone booth, elevator car, train compartment, airplane compartment, automobile interior, subway compartment, and the like. While not as dramatic of an impact as green apple, seashore and cucumber odorant substances can also be used to increase or expand the perception of room size.

It was further found that administration of a barbecue smoke odorant substance will diminish perception of room size or space of an area, for a person suffering from agoraphobia or other like phobia. A barbecue smoke odorant can therefore be used to reduce the anxiety felt by a person suffering from agoraphobia, and/or reduce the stress experienced by a person with a mild spatial dissonance of open space such as a convention hall, interior of a mall, hallway, concert hall, out-of-doors expanse, and the like.

Such odorants are commercially available, for example, from International Flavors and Fragrances, Inc. (IFF), New York, N.Y.

According to the invention, the odorant substance is dispensed in an amount and time effective to provide a vaporous emission for inhalation by the patient to effectively change the patient's perception of space and reduce anxiety of the patient having a stress reaction due to a spatial dissonance. Such an effect can be assessed and measured subjectively by interviewing and questioning the patient about their perception of relative space before and after the administration of the odorant substance, and assessing their response according to an analog rating scale, for example, a scale of 1–5 wherein 1=confined and 5=roomy.

The odorant can be dispensed by means of a scented cloth such as a fragranced surgical mask, a vessel containing the odorant substance, optionally with a valve and nozzle mechanism for dispensing the substance, a blister pack containing a preparation of the odorant, an aerosol or non-aerosol spray, a gas, a solid or liquid air freshener, a scented cloth, lotion, cream, perfume, cologne, potpourri, incense, lightbulb ring, a candle, fabric softener, carpet shampoo or freshener, a plug-in air freshener, scratch-andsniff odor patches containing microcapsules of the odorant, and the like. The odorant substance can be administered in combination with an odorless liquid carrier such as mineral oil or water, and can be formulated with a viscosity effective to allow for aerosolization.

The odorant can be provided in a portable dispenser for ready individual use, for example, by means of a blister pack, a small vial of lotion, a booklet of scratch-and-sniff odor patches, and the like, that include an effective amount of the desired odorant substance. An odorant substance can also be administered to a group of people within a confined area, for example, by pumping air containing the odorant substance through an air vent, spraying the odorant substance into the air as a mist or dry powder using an aerosol or non-aerosol spray, or by placing the odorant substance as a solid or liquid in the room such as a solid or liquid air freshener, scented candle, carpet freshener, and the like.

The odorant substance can be packaged as a part of an article of manufacture, or kit. The kit can include in association, for example, (a) the odorant substance, carrier and other optional additives for forming a composition, placed in containing means such as a vial, jar, pouch, can, bottle, cloth, aerosol can, blister pack, and the like, containing an effective amount of the odorant substance; and (b) means for instructing as to the odorant substance and its use for treating a spatial dissonance to alter a perception of room size. The parts of the kit can be contained or separately packaged within a packaging material, such as a box or bag.

EXAMPLE

Subject evaluation.

Eight subjects, four females and four males, aged 18 to 64 years (mean =30.9, median 19), underwent a series of olfactory and psychological tests. Formal olfactory tests included Pyridine Threshold Test of Amoore, Unilateral Thiophane Threshold Test of Amoore, and the University of Pennsylvania Smell Identification Test (Hirsch et al., *Chemical Senses* 17: 643 (1992); Amoore et al., *Rhinology* 21:49–54 (1983); and Doty et al., *Chemical Senses* 10:297–300 (1985), respectively). All were performed according to standard test procedures.

Olfactory test results were as follows: on the threshold test of Amoore, five subjects scored 100%, two scored 90%, and one scored 80%. UPSIT scores ranged from 19 to 37. Subject number 2 scored hyposmic (diminished sense of smell) on this test as adjusted for age and sex. The seven remaining subjects had UPSIT scores ranging from 29 to 37 (TABLE 1). Olfactory threshold ranged from −5 to 20 decismels with an average for the left nostril of 11.9 and for the right nostril of 10 decismels, all within the normal range (TABLE 1).

TABLE 1

OLFACTORY TEST SCORES

| Subject | 1 | 2 | 3 | 4 | 5 | 6 | 7 | 8 |
|---|---|---|---|---|---|---|---|---|
| Threshold Tests of Amoore | | | | | | | | |
| Score UPSIT | 90% | 100% | 100% | 100% | 100% | 90% | 80% | 100% |
| Score Olfactory Threshold | 36 | 19* | 29 | 35 | 36 | 37 | 37 | 34 |
| Right | −5 | 15 | 20 | 10 | 10 | 5 | 15 | 10 |
| Left | 15 | 10 | 10 | 10 | 15 | 5 | 20 | 10 |

*Hyposmic

The following standardized self evaluations were also administered: Zung Self-Rating Depression Scale, Zung Anxiety Inventory, and Beck Depression Inventory (W. W. K. Zung, *Arch. Gen. Psychiatry* 12:63–70 (1965); W. W. K. Zung, *Psychosomatics* 12(6):371–379 (1971); Beck et al., "Assessment of Depression, Depression Inventory: Psychological Measurements in Psychopharmacology," in *Modern Problems in Psychopharmacology* (9th ed.), Pinchot et al. (ed.) (1974), respectively). Claustrophobia, phobia, and spatial anxiety were assessed using detailed self-evaluation questionnaires devised from a checklist integrating criteria specified by DSM-IV for diagnoses of panic disorder, anxiety disorders, and specific phobia (American Psychiatric Association, *Diagnostic and Statistical Manual of Mental Disorders* (4th ed.), at pages 393–444, Washington, D.C., American Psychiatric Association (1994)). The subjects were also assessed according to standard questionnaires including Anxiety Status Inventory and the SCL-90R (Bystritsky et al., "Development of a Multidimensional Scale of Anxiety," *J. of Anxiety Disorders* (19___); L. R. Derogatis, The SCL-90R, Baltimore Clinical Psychometric Research (1977)). Also used was a compendium of several questionnaires based on claustrophobia (C. B. Scrignar, "Stress Strategies," *The Treatment of the Anxiety Disorders*, pages 6–7, S. Karger Basel (1983); Clarke et al., *Hypnosis and Behavior Therapy, The Treatment of Anxiety and Phobias*, pages 320–321, Springer Publishing Company, New York, N.Y. (1983); World Psychiatric Association, *Panic Anxiety and its Treatments*, page 7, Klerman et al. (eds.), American Psychiatric Press, Inc., Washington, D.C. (1993)). The questionnaire on claustrophobia also included a differentiation between "suffocating" and "restricting" claustrophobia (Rachman et al., "Analyses of Claustrophobia," *J. Anxiety Disorders*, pages 281–291, Pergamon Press Ltd. (1993)).

The psychological test scores showed that four subjects were at least somewhat anxious, of which one was depressed and another was slightly to moderately depressed (TABLE 2). Zung anxiety scores averaged 34.5 and ranged from 20 to 42 (less than 36 being normal). Zung depression scores averaged 34.4 and ranged from 24 to 46 (less than 40 being normal). Beck depression scores averaged 6.6 and ranged from 0 to 16 (14 or less being normal).

TABLE 2

PSYCHOLOGICAL TEST SCORES

| | Subjects | | | | | | | |
|---|---|---|---|---|---|---|---|---|
| | 1 | 2 | 3 | 4 | 5 | 6 | 7 | 8 |
| *Zung Anxiety | <u>39</u> | 20 | <u>42</u> | <u>37</u> | 32 | <u>42</u> | 33 | 31 |
| **Zung Depression | 35 | 24 | <u>43</u> | 32 | 33 | <u>46</u> | 34 | 25 |
| ***Beck Depression | 11 | 0 | 10 | 6 | 4 | <u>16</u> | 4 | 2 |

*Normal = <36.
**Normal = <40.
***Normal = 14 or less.

Of the eight subjects, four were single. While one smoked cigarettes, none used drugs or medications.

In assessing individual variations in smell awareness, subjects were queried as to their perceptions of both their own personal odor and the odors around them, as well as their use of cosmetic and hygienic fragrances. One subject considered his sense of smell as excellent, while all others described their olfactory ability as normal. On a scale from 1–10, with 10 being the highest, subjects rated the importance of their sense of smell as 7 on average, with a range of 3–10.

In assessing perception of personal odor, five characterized the odor about them as pleasant, and three subjects considered their own smell as neutral or provided no response to the question. The general perception of a pleasant self odor correlated with personal fragrancing. Six of the eight subjects used commercial perfumes or colognes, and breath fresheners including mints and mouthwash, while two did not. In addition, while all eight subjects used a deodorant, the six subjects who used a perfume or cologne also used a scented deodorant. The two subjects who used no perfume, used an unscented deodorant.

The subjects were also questioned about external odors (those not from their natural body odor or personal fragrancing). Five subjects considered persons around them as having a pleasant smell, two were neutral about other people's odors and one subject perceived people around them as having an unpleasant smell. When questioned about the use of potpourri or room fresheners, four subjects were found to use such fresheners, three did not, and one gave no response.

Collection of Data

To assess initial perceptions of spatial size, the subjects completed a questionnaire including a 9-centimeter analog scale to rate the feeling of room size. This was performed twice, each time in a clinically odor-free environment: once in a 12 ft. by 9 ft. by 9 ft. examining room, and a second time in a cylindrical space-deprivation booth 2.5 ft. in diameter by 4.5 ft. in height. After sitting confined for one minute in the booth, subjects then donned unfragranced surgical masks. After 30 seconds wearing the masks, they again completed the analog scale. The masks were then removed for a two-minute odorless hiatus in the booth. The same procedure was repeated ten times using surgical masks with ten different fragrances applied.

The following fragrances were tested: evergreen (International Flavors and Fragrances, Inc. (IFF)); barbecue smoke (IFF 2247-HS); Tranquilities perfume (Elizabeth Arden); vanilla (Florasynth, Inc., New York, N.Y.; AE-3899); buttered popcorn (Florasynth; AG-6958 (GRAS) ); seashore (IFF); charcoal-roasting meat combination (IFF 2189-HS); cucumber (IFF); coconut (IFF); and green apple (IFF).

One to two drops of each odorant were placed on each surgical mask, producing odor levels considered hedonically acceptable by a sensory panel consisting of staff from the Smell & Taste Treatment and Research Foundation. Although the odorant substance was administered using a fragranced surgical mask in the experiment, it is understood that a variety of shapes, sizes and configurations may be accommodated for the administration of the odorant substance according to the invention.

The perfumed masks were presented in a random, double-blind manner. Afterwards, subjects rated the familiarity of the odors and their hedonics (pleasant or unpleasant) on analog scales. Following testing of a fragrance mask, another unfragranced mask was applied for evaluation. Statistical analysis was then performed based on Signed-Rank test for pair differences (E. L. Lehmann, *Nonparametrics: Statistical Methods Based on Ranks*, Holden-Day (1975)).

Odors were classified two ways: "indoor" versus "outdoor" (TABLE 3), and as "food" versus "nonfood" (TABLE 4).

TABLE 3

CLASSIFICATIONS OF ODORS

| Indoor | Outdoor |
| --- | --- |
| Barbecue Smoke | Evergreen |
| Vanilla | Tranquilities |
| Buttered Popcorn | Seashore |
| Charcoal Roasting Meat | Cucumber |
|  | Coconut |
|  | Green Apple |

TABLE 4

CLASSIFICATIONS OF ODORS

| Food | Non-Food |
| --- | --- |
| Barbecue Smoke | Evergreen |
| Vanilla | Tranquilities |
| Buttered Popcorn | Seashore |
| Charcoal Roasting Meat | Green Apple |
| Cucumber |  |
| Coconut |  |

The effect of each odor on perception of room size was calculated for each of the eight subjects. This was done by first computing the average score on analog scales of room size for the two blank masks. This average score was then used as a baseline from which to determine the shift due to the presence of each of the odors (TABLE 5). This odor-induced shift was also calculated for the seven subjects defined as normosmics (having a normal sense of smell) based on the UPSIT and for the six subjects who were found to use personal fragrancing.

TABLE 5

EIGHT SUBJECTS' SHIFTS ON ANALOG SCALE OF ROOM SIZE WITH TEN ODORS

| Odors | Subjects | | | | | | | |
| --- | --- | --- | --- | --- | --- | --- | --- | --- |
|  | 1 | 2 | 3 | 4 | 5 | 6 | 7 | 8 |
| Evergreen | −.25 | 0 | −1 | −2.5 | 2 | .25 | 2.5 | .5 |
| Barbecue Smoke | −.25 | 0 | −1 | −.5 | −1 | −.25 | −1 | .5 |
| Tranquilities | .25 | 0 | 0 | −2 | 0 | −.75 | 3 | .5 |
| Vanilla | .25 | 0 | −1 | −1.5 | −1 | −.75 | 3 | 0 |
| Buttered Popcorn | −.25 | 0 | 0 | −2.5 | −.5 | −.25 | 3.5 | .5 |
| Seashore | −.25 | 0 | −.5 | −2 | .5 | −.75 | 2.5 | 2 |
| Charcoal Roasting Meat | −.25 | 0 | .5 | −1.5 | −.5 | −.75 | 2.5 | .5 |
| Cucumber | −.25 | 0 | −1 | −1.5 | −1 | .25 | 3 | 0 |
| Coconut | −.25 | 0 | −.5 | 2 | −2 | −.25 | −3 | .5 |
| Green Apple | −.25 | 0 | .5 | −.5 | 1.5 | .25 | 3 | .5 |
| Subjects Characteristics | | | | | | | | |
| Age |  |  |  |  |  |  |  |  |
| Sex |  |  |  |  |  |  |  |  |
| Good ability to smell | Yes | No | Yes | Yes | Yes | Yes | Yes | Yes |
| Use perfume | No | No | Yes | Yes | Yes | Yes | Yes | Yes |

For each subject, a change from baseline was detected for each odor. Additionally for each subject, the change from baseline of each odor was contrasted with the median change from baseline for the other nine odors tested. In this fashion, every odor was tested for each individual. Hence, for each individual, calculations were made for the difference between the analog shift for each odor and the mean of the analog shifts for the other nine odors.

The median change for each odor from calculated baselines for each subject was determined. The same method was used to find the median for the other nine odors across all subjects. Then the significance of this difference was determined between these medians (TABLE 6). In a similar fashion, significance was determined for all normosmic subjects as determined by the UPSIT (n=7) (TABLE 7), and for those who used personal fragrancing (n=8) (TABLE 8).

Further, medians were also compared differentiating odors based on hedonics, recognition, and odor classification (i.e., indoor versus outdoor, food versus nonfood) for all subjects, normosmics and those using personal fragrancing, and p-values were computed in the same manner (TABLE 9).

TABLE 6

COMPARISONS OF MEDIANS OF ODOR SHIFTS FROM BASELINE VERSUS MEDIANS OF BASELINE SHIFTS FOR THE OTHER NINE ODORS ALL SUBJECTS (n = 8)
Each odor versus all others:

| Odor | Signed-Rank Test p-value |
| --- | --- |
| Evergreen | .9844 |
| Barbecue Smoke | .0469* |
| Tranquilities | .5469 |
| Vanilla | .8438 |
| Buttered Popcorn | .7427 |
| Seashore | .5469 |
| Charcoal Roasting Meat | .9453 |
| Cucumber | .9453 |
| Coconut | .7427 |
| Green Apple | .1484 |

*Significantly lower than the average of all others

TABLE 7

COMPARISONS OF MEDIANS OF ODOR SHIFTS FROM BASELINE VERSUS MEDIANS OF BASELINE SHIFTS FOR THE OTHER NINE ODORS NORMOSMIC SUBJECTS AS DETERMINED BY UPSIT (n = 7)
Each odor versus all others:

| Odor | Signed-Rank Test p-value |
| --- | --- |
| Evergreen | .9844 |
| Barbecue Smoke | .0625* |
| Tranquilities | .1563 |
| Vanilla | .8125 |
| Buttered Popcorn | .2969 |
| Seashore | .1563 |
| Charcoal Roasting Meat | .4688 |
| Cucumber | .6875 |
| Coconut | 1.0000 |
| Green Apple | .0156** |

*Lower, but no longer significantly lower than the others.
**Significantly higher than the average of all the others.

TABLE 8

COMPARISONS OF MEDIANS OF ODOR SHIFTS FROM BASELINE VERSUS MEDIANS OF BASELINE SHIFTS FOR THE OTHER NINE ODORS SUBJECTS WHO USE PERSONAL FRAGRANCE (n = 6)
Each odor versus all others:

| Odor | Signed-Rank Test p-value |
| --- | --- |
| Evergreen | 1.0000 |
| Barbecue Smoke | .0938* |
| Tranquilities | .3125 |
| Vanilla | 1.0000 |
| Buttered Popcorn | .4375 |
| Seashore | .2188 |
| Charcoal Roasting Meat | .5625 |
| Cucumber | .8438 |
| Coconut | .8438 |
| Green Apple | .0313** |

*Lower, but not significantly lower than the others.
**Significantly higher than the average of all the others.

TABLE 9

P-VALUES FROM THE SIGNED-RANK TEST FOR PAIRED DIFFERENCES

| | All Subjects | Normosmics | Personal Fragrance Users |
| --- | --- | --- | --- |
| Like vs. Dislike | .3125 | .3125 | .4375 |
| Recognize vs. Fail to Recognize | .1563 | .1563 | .1875 |
| Indoor vs. Outdoor | .2031 | .2031 | .1563 |
| Food vs. NonFood | .1563 | .1563 | .2188 |

Data Analysis

TABLE 5 shows the shift with each odor away from the average with the odorless masks. Those with positive values made the room appear larger and those with negative values made the room subjectively smaller compared to the non-odorized condition. The odor that caused a perceptual shift that was statistically significant was the odor of barbecue smoke ($p<0.05$) which decreased the perceived size of the room.

Data was further analyzed excluding the hyposmic individual, subject 2, (UPSIT rated microsmic) and also for the six subjects who used personal fragrances (subjects 3 through 8). In both these subgroups (normosmics and personal-fragrance users), the green apple odor increased perceptions of room size. In both groups, green apple odor produced statistically significant results: in all normosmics ($p=0.03$) and in normosmic fragrance users ($p=0.02$).

The green apple odor had the most significant impact of enlarging perception of room size. Seashore and cucumber had similar effects on perception although less significant than the effect provided by the green apple odorant.

The odors had no effect on the perception of room size by the individual with poor olfactory ability based on the UPSIT. This indicates that the odors did in fact cause response to room size perception.

Thus, the invention has been described with reference to various specific and preferred embodiments and techniques. However, it should be understood that many variations and modifications may be made while remaining within the spirit and scope of the invention, and the invention is not to be construed as limited to the specific embodiments shown in the drawings.

What is claimed is:

1. A method for altering a person's perception of relative space of a confined area, comprising:

administering to the person an effective amount of a green apple odorant such that the relative space of the area is perceived to diminish.

2. The method of claim 1, wherein the confined area is selected from the group consisting of a room, closet, telephone booth, elevator car, train compartment, airplane compartment, automobile interior, subway compartment.

3. The method of claim 1 further comprising questioning the person before and after administering the odorant to assess the effect of the odorant on the person's perception of the area.

4. The method of claim 1, wherein the method comprises administering the odorant in a form selected from the group consisting of a spray, gas, scented cloth, lotion, cream, perfume, cologne, scratch-and-sniff odor patch containing microcapsules of the odorant, a blister pack containing the odorant, solid air freshener, potpourri, incense, lightbulb ring, candle, fabric softener, carpet freshener, and combinations thereof.

5. The method of claim 1, wherein the method comprises administering the odorant to a group of patients.

6. The method of claim 1, wherein the method comprises administering the odorant by pumping a gas containing the odorant through an air vent into a room.

7. The method of claim 1, wherein the method comprises administering the odorant by spraying the odorant substance into the air.

8. The method of claim 1, wherein the method comprises administering the odorant in combination with an odorless liquid carrier.

9. The method of claim 8, wherein the viscosity of the odorant in the carrier is effective to allow for aerosolization, and the method comprises administering the odorant by spraying the odorant substance.

10. A method for altering a person's perception of relative space of an area, comprising:
administering to the person an effective amount of a barbecue smoke odorant such that the relative space of the area is perceived to diminish.

11. The method of claim 10, wherein the area is selected from the group consisting of a convention hall, interior of a mall, hallway, concert hall, a roadway.

12. The method of claim 10, further comprising questioning the person before and after administering the barbecue smoke odorant to assess the effect of the odorant on the person's perception of the area.

13. The method of claim 10, wherein the method comprises administering the odorant in a form selected from the group consisting of a spray, gas, scented cloth, lotion, cream perfume, cologne, scratch-and-sniff odor patch containing microcapsules of the odorant, a blister pack containing the odorant, solid air freshener, potpourri, incense, lightbulb ring, candle, fabric softener, carpet freshener, and combinations thereof.

14. The method of claim 10, wherein the method comprises administering the odorant to a group of patients.

15. The method of claim 10, wherein the method comprises administering the odorant by pumping a gas containing the odorant through an air vent into a room.

16. The method of claim 10, wherein the method comprises administering the odorant by spraying the odorant substance into the air.

17. The method of claim 10, wherein the method comprises administering the odorant in combination with an odorless liquid carrier.

18. The method of claim 17, wherein the viscosity of the odorant in the carrier is effective to allow for aerosolization, and the method comprises administering the odorant by spraying the odorant substance.

* * * * *

UNITED STATES PATENT AND TRADEMARK OFFICE
CERTIFICATE OF CORRECTION

PATENT NO.: 5,759,521

DATED: June 2, 1998

INVENTOR(S): Alan R. Hirsch

It is certified that error appears in the above-identified patent and that said Letters Patent is hereby corrected as shown below:

At col. 8, claim 1, the phrase "such that the relative space of the area is perceived to diminish." should read as --such that the relative space of the area is perceived to expand.--

Signed and Sealed this

Fifteenth Day of June, 1999

Attest:

Q. TODD DICKINSON

*Attesting Officer*  *Acting Commissioner of Patents and Trademarks*